United States Patent
Zhang et al.

(10) Patent No.: US 11,020,023 B2
(45) Date of Patent: Jun. 1, 2021

(54) METHOD AND APPARATUS FOR ESTIMATING THE FALL RISK OF A USER

(71) Applicant: KONINKLIJKE PHILIPS N.V., Eindhoven (NL)

(72) Inventors: Wei Zhang, Eindhoven (NL); Warner Rudolph Theophile Ten Kate, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 386 days.

(21) Appl. No.: 14/648,266

(22) PCT Filed: Nov. 25, 2013

(86) PCT No.: PCT/IB2013/060371
§ 371 (c)(1),
(2) Date: May 29, 2015

(87) PCT Pub. No.: WO2014/083490
PCT Pub. Date: Jun. 5, 2014

(65) Prior Publication Data
US 2015/0313552 A1 Nov. 5, 2015

Related U.S. Application Data

(60) Provisional application No. 61/731,599, filed on Nov. 30, 2012.

(51) Int. Cl.
*A61B 5/00* (2006.01)
*A61B 5/11* (2006.01)
*G16H 50/30* (2018.01)

(52) U.S. Cl.
CPC .......... *A61B 5/1117* (2013.01); *A61B 5/6801* (2013.01); *A61B 5/7246* (2013.01);
(Continued)

(58) Field of Classification Search
None
See application file for complete search history.

(56) References Cited

U.S. PATENT DOCUMENTS 8,109,890 B2 * 2/2012 Kamiar ................ A61B 5/6828
600/595
8,206,325 B1 * 6/2012 Najafi ................... A61B 5/1116
600/587
(Continued)

FOREIGN PATENT DOCUMENTS

EP 1195139 A1 4/2002
JP 2008173249 A 7/2008
(Continued)

OTHER PUBLICATIONS

Zijlstra et al.: Sit-stand and stand-sit transitions in older adults and patients with Parkinson's disease: event detection based on motion sensors versus force plates. Journal of NeuroEngineering and Rehabilitation 2012 9:75 | DOI: 10.1186/1743-0003-9-75.*
(Continued)

*Primary Examiner* — Patrick Fernandes
*Assistant Examiner* — Benjamin S Melhus

(57) ABSTRACT

There is provided a method of estimating the fall risk of a user, the method comprising analyzing measurements of the acceleration of the user to determine if the user has performed a sit-to-stand transfer; identifying the peak vertical acceleration of the user during the sit-to-stand transfer from the measurements of the acceleration of the user; and estimating a fall risk for the user from the identified peak vertical acceleration.

19 Claims, 8 Drawing Sheets

(52) U.S. Cl.
CPC ........... *A61B 5/7275* (2013.01); *G16H 50/30* (2018.01); *A61B 2560/0257* (2013.01); *A61B 2562/0219* (2013.01)

(56) References Cited

U.S. PATENT DOCUMENTS

| | | | |
|---|---|---|---|
| 2004/0015103 A1* | 1/2004 | Aminian | A61B 5/1127 600/595 |
| 2008/0288200 A1* | 11/2008 | Noble | A63B 24/0062 702/96 |
| 2009/0048540 A1* | 2/2009 | Otto | A61B 5/6831 600/595 |
| 2009/0322540 A1* | 12/2009 | Richardson | A61B 5/411 340/573.7 |
| 2011/0144542 A1* | 6/2011 | Jin | A61B 5/0002 600/595 |
| 2012/0232823 A1 | 9/2012 | Baggen et al. | |
| 2013/0303860 A1* | 11/2013 | Bender | A61B 5/1117 600/300 |
| 2014/0191863 A1* | 7/2014 | Ten Kate | A61B 5/02055 340/539.12 |
| 2014/0375461 A1* | 12/2014 | Richardson | A61B 5/681 340/573.7 |
| 2016/0100776 A1* | 4/2016 | Najafi | A61B 5/7225 600/595 |
| 2016/0346614 A1* | 12/2016 | Kirby | A63B 71/06 |
| 2017/0042453 A1* | 2/2017 | Cheung | A61B 5/117 |

FOREIGN PATENT DOCUMENTS

| | | |
|---|---|---|
| RU | 122009 U1 | 11/2012 |
| WO | 0228282 A1 | 4/2002 |
| WO | 2010035187 A1 | 4/2010 |
| WO | 2010035191 A2 | 4/2010 |
| WO | 2010044013 A1 | 4/2010 |
| WO | 2013001411 A1 | 1/2013 |

OTHER PUBLICATIONS

Zijlstra et al: "A Body-Fixed-Sensor-Based Analysis of Power During Sit-to-Stand Movements"; Gait & Posture 31 (2010), pp. 272-278.

Sableman et al: "Upper Body Motion Analysis for Amelioration of Falls in the Elderly"; 1996 Rehabilitation R&D Center Progress Report, 3 Page Document.

Redmond et al: "Automatic Segmentation of Triaxial Accelerometry Signals for Falls Risk Estimation"; 32nd Annual International Conference of the IEEE EMBS, Buenos Aires, Argentina, Aug. 31-Sep. 4, 2010, pp. 2234-2237.

Ganea et al: "Mulit-Parametric Evaluation of Sit-to-Stand and Stand-to-Sit Transitions in Elderly People"; Medical Engineering & Physics 33 (2011), pp. 1086-1093.

* cited by examiner

METHOD AND APPARATUS FOR ESTIMATING THE FALL RISK OF A USER

CROSS-REFERENCE TO PRIOR APPLICATIONS

This application is the U.S. National Phase application under 35 U.S.C. § 371 of International Application No. PCT/2013/060371, filed on Nov. 25, 2013, which claims the benefit of U.S. Provisional Patent Application No. 61/731,599, filed on Nov. 30, 2012. These applications are hereby incorporated by reference in their entirety herein.

TECHNICAL FIELD OF THE INVENTION

The invention relates to a method and apparatus for estimating the fall risk of a user, and in particular relates to a method and apparatus that estimates the fall risk of a user based on an analysis of a sit-to-stand transfer movement by the user.

BACKGROUND TO THE INVENTION

Falls are one of the greatest health risk factors for elderly people. About one third of older people above the age of 65 fall at least once a year.

Many of these falls could be avoided by early identification of fall risk and the application of effective and targeted fall prevention programs.

Fall prevention trials based on strength and balance training (SBT) have shown that the risk of falling for elderly people can be reduced. Balance performance measures can be used as early indicators of fall risk, and also to measure the progress of fall prevention programs. The 'sit-to-stand' (STS) transfer has been identified as one important movement which can be used as a balance performance measure and thus a measure of fall risk. In daily life, a person performs the STS transfer many times a day.

Conventionally, clinical measurement systems (such as those including a force plate and an optical marker system) are used to provide an accurate quantification of power during a sit-to-stand transfer. In these measurement systems, the force plate provides the vertical ground reaction force and the optical marker system provides a measure of displacement in three dimensions. The combination of both measurements is used to quantify the power during a sit-to-stand transfer.

These measurement systems have several drawbacks. Firstly, they are clinical equipment, which requires the user to attend a clinic. Preparing for and performing measurements is labor intensive (particularly if optical markers need to be attached to specific parts of the body). In addition, they only provide a snapshot of the user's balance performance, where, owing to the clinical setting, the user commonly performs above their average capability. Finally, the measurement systems involve a procedure which is quite cumbersome for the user.

Fall risk assessment in the home environment is usually carried out by a telephone interview or by self-reporting from the user themselves, but these assessments are not particularly reliable.

However, recent advances in on-body sensors have improved home-based fall risk assessment application/tools. The power of sit-to-stand transfers can be derived using an on-body sensing platform that includes accelerometers. One such system is described in WO 2010/035187.

Experiments have shown that the power exercised during a STS as measured with an accelerometer correlates with that measured using a force plate in the standard clinical assessment. However, a disadvantage of that method is that it requires a good delineation of the start and end times of the STS transfer, since these times affect the outcome of the computation. In particular the start time will affect the maximal power that is identified, since it has an effect on the integration that has to be applied to the accelerometer signal in order to derive power.

In a clinical or laboratory setting, this problem is less critical, since the start and end times can be determined through observation of the user as they perform the STS. Analysis of the signal can be performed with assistance from these observations. Also, the acceleration signal around the STS transfer is less noisy as it would be in a daily life situation. This also helps the delineation as well as reducing the influence of errors in the delineation. Outside of the clinical setting (e.g. in daily life), this observation is absent, and delineation is a problem. In addition, the acceleration signal will be more noisy. It is possible for the user to manually indicate the start and/or end of the transfer, for example by pressing a button at the onset or end of the STS, but this means that the system is not unobtrusive.

Therefore, there is a need for an improved method and apparatus for estimating a fall risk through the analysis of a sit-to-stand transfer.

SUMMARY OF THE INVENTION

It has been found that there is a high linear correlation between the peak vertical acceleration that occurs during a sit-to-stand transfer and the peak power generated by the user during the transfer. This correlation is shown in FIG. 1 which plots the peak power during a sit-to-stand transfer against the peak vertical acceleration for several variations of the sit-to-stand movement for a number of different users. In this figure, both the acceleration and power have been scaled and normalized with respect to gravity. The variations of the sit-to-stand transfer include a normal speed transfer (NormSTS), a normal speed transfer in which the user does not use their arms (NormSTSwithoutArms), a faster transfer (FastSTS), and transfers that occur as part of a fast and normal speed timed-up-and-go (TUG) test, where the user has to stand up, walk and return to the sitting position (labeled STSinFastTUG and STSinNormTUG respectively).

The graphs in FIG. 2 illustrate that peak vertical acceleration exhibits the same sensitivity to fall risk as peak power. In particular, the left hand side of FIG. 2(a) shows an analysis of the variance of the peak vertical acceleration values (scaled for gravity) that are found for healthy (i.e. low fall risk) users, and the right hand side shows an analysis of the variance of the peak vertical acceleration values (scaled for gravity) that are found for frail (i.e. high fall risk) users. FIG. 2(b) shows the corresponding analysis of variance for peak power, and thus it can be seen that peak vertical acceleration during a sit-to-stand transfer provides similar information on the fall risk of the user as peak power.

Thus, the invention exploits the finding that the peak vertical acceleration during a sit-to-stand transfer provides a useful measure of the fall risk of the user. In particular, according to a first aspect of the invention, there is provided a method of estimating the fall risk of a user, the method comprising analyzing measurements of the acceleration of the user to determine if the user has performed a sit-to-stand transfer; identifying the peak vertical acceleration of the user during the sit-to-stand transfer from the measurements of the acceleration of the user; and estimating a fall risk for the user from the identified peak vertical acceleration.

In preferred embodiments, the identified peak vertical acceleration is scaled using an estimate of gravity obtained from the measurements of the acceleration of the user and the scaled peak vertical acceleration is used to estimate the fall risk for the user. Calibration errors in the sensor measurements can introduce errors into the peak vertical acceleration and thus the assessment of fall risk. Therefore, scaling the peak vertical acceleration in this way means that the calibration errors can be removed from the sensor measurements.

In a preferred embodiment, the method further comprises the steps of estimating acceleration due to gravity from the measurements of the acceleration of the user; and subtracting the estimated acceleration due to gravity from the identified peak vertical acceleration to give a scaled peak vertical acceleration.

In an alternative embodiment, the method further comprises the steps of estimating acceleration due to gravity from the measurements of the acceleration of the user; and subtracting the estimated acceleration due to gravity from the measurements of the acceleration of the user to give scaled measurements of the acceleration of the user; wherein the step of identifying the peak vertical acceleration of the user during the sit-to-stand transfer comprises identifying the peak vertical acceleration of the user from the scaled measurements of the acceleration.

Preferably, the estimate of gravity is obtained from the measurements of acceleration by averaging a plurality of the measurements of acceleration occurring in a time period before the start of the sit-to-stand transfer to give the estimate of gravity.

In some embodiments, the estimate of gravity is obtained from the measurements of acceleration in a time period before the start of the sit-to-stand transfer only if the standard deviation, variance or range of the plurality of measurements of acceleration occurring in the time period is less than a threshold value.

In some embodiments, the scaled peak vertical acceleration is normalized using the estimate of gravity, and the normalized scaled peak vertical acceleration is used to estimate the fall risk for the user.

In preferred implementations, the measurements of the acceleration of the user are obtained using one or more accelerometers attached to or worn by the user.

In alternative implementations, the measurements of the acceleration of the user are obtained using a force plate that measures the forces generated by the user during movement.

In some embodiments, the method comprises performing the step of identifying for a plurality of sit-to-stand transfers, and wherein the step of estimating the fall risk comprises determining the fall risk from an average of the peak vertical accelerations identified for the plurality of sit-to-stand transfers.

In some embodiments, the step of estimating the fall risk comprises determining the fall risk from the average of the peak vertical accelerations identified for the plurality of sit-to-stand transfers and an indication of the number of times that the user performed the sit-to-stand transfer in a specified time period.

Some embodiments further comprise the step of comparing the estimated fall risk to one or more previously estimated fall risks to determine a fall risk trend for the user.

According to a second aspect of the invention, there is provided a computer program product, comprising computer program code that, when executed on a computer or processor, causes the computer or processor to determine a fall risk for a user by analyzing measurements of the acceleration of the user to determine if the user has performed a sit-to-stand transfer; identifying the peak vertical acceleration of the user during the sit-to-stand transfer from the measurements of the acceleration of the user; and estimating a fall risk for the user from the identified peak vertical acceleration.

In preferred embodiments, the computer program product is further configured to cause the computer or processor to scale the identified peak vertical acceleration using an estimate of gravity obtained from the measurements of the acceleration of the user, and to use the scaled peak vertical acceleration to estimate the fall risk for the user.

Various other embodiments of the computer program product are also contemplated in which the computer program code is further configured to cause a computer or processor to perform any of the above-described methods.

According to a third aspect of the invention, there is provided an apparatus for estimating a fall risk for a user, the apparatus comprising a processing unit configured to analyses measurements of the acceleration of the user to determine if the user has performed a sit-to-stand transfer; identify the peak vertical acceleration of the user during the sit-to-stand transfer from the measurements of the acceleration of the user; and estimate a fall risk for the user from the identified peak vertical acceleration.

In preferred embodiments, the processing unit is configured to scale the identified peak vertical acceleration using an estimate of gravity obtained from the measurements of the acceleration of the user and to use the scaled peak vertical acceleration to estimate the fall risk for the user.

Various other embodiments of the apparatus are also contemplated in which the processing unit is further configured to execute any of the above-described method steps.

According to a fourth aspect of the invention, there is provided a device that is configured to be worn by a user, the device comprising an accelerometer that measures the acceleration acting on the device in three dimensions; and an apparatus as described above, wherein the processing unit is configured to process the measurements of the acceleration from the accelerometer.

According to a fifth aspect of the invention, there is provided a system that comprises a device that is configured to be worn by a user, the device comprising an accelerometer that measures the acceleration acting on the device in three-dimensions; and a base unit that is configured to communicate with the device, and that comprises an apparatus as described above, wherein the processing unit is configured to process the measurements of the acceleration from the accelerometer.

According to a sixth aspect of the invention, there is provided a system that comprises a force plate; and a base unit that comprises an apparatus as described above, wherein the processing unit is configured to receive measurements of forces from the force plate and to process the measurements of forces to determine measurements of the acceleration.

According to a seventh aspect of the invention, there is provided a method of estimating the fall risk of a user, the method comprising analyzing measurements of the acceleration of the user to determine if the user has performed a sit-to-stand transfer; identifying the peak vertical acceleration of the user during the sit-to-stand transfer from the measurements of the acceleration of the user, wherein the identified peak vertical acceleration is scaled using an estimate of gravity obtained from the measurements of the acceleration of the user; and estimating a fall risk for the user from the scaled peak vertical acceleration.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 3:
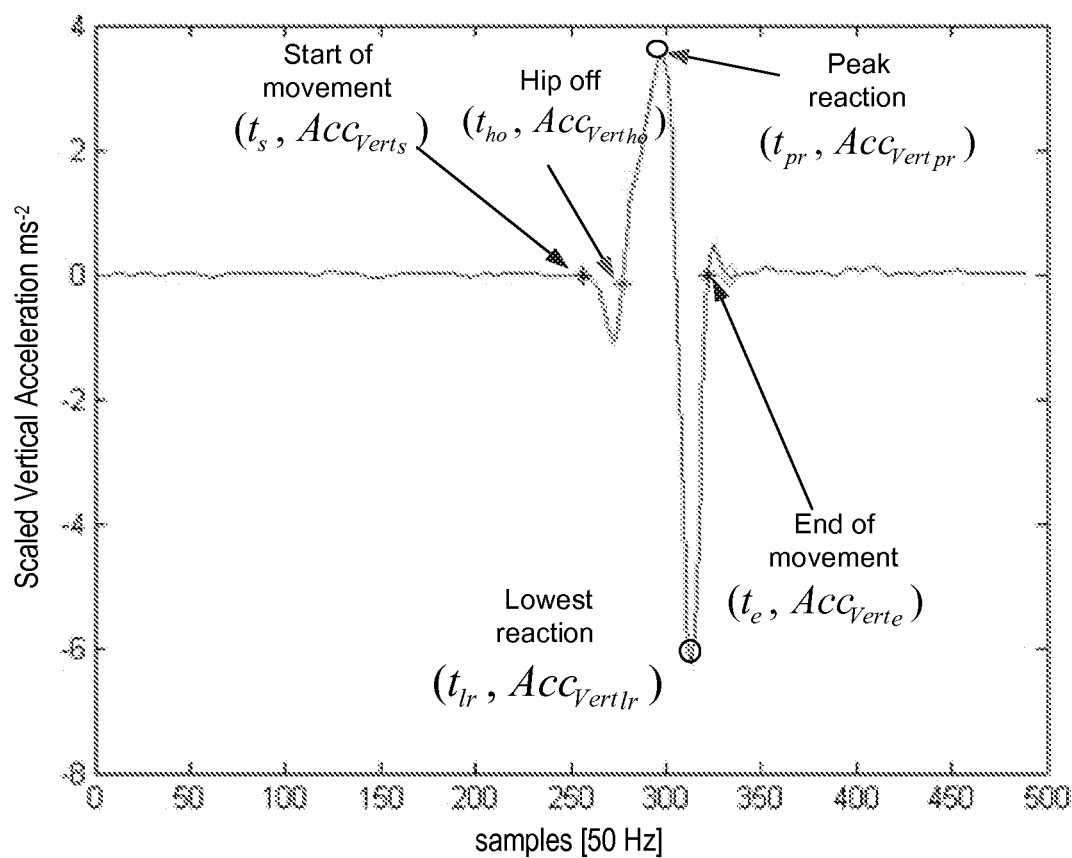
FIG. 3 is a graph illustrating an example of the variation in vertical acceleration during a sit-to-stand transfer.

The graph in FIG. 3 shows the vertical acceleration during a typical sit-to-stand motion (which has been scaled to exclude acceleration due to gravity). The user starts from rest (i.e. the measured acceleration in the vertical direction due to motion of the user is approximately 0) and the user begins to move at time $t_s$. The acceleration measured at this time is denoted $Acc_{vert\_s}$. There is typically a small minimum in the acceleration profile just after the user starts to move and before they rise off their chair. Subsequently, the user's hip leaves the means of support (i.e. chair) at time $t_{ho}$ ('ho' represents hip off), and the acceleration at this time is denoted $Acc_{vert\_ho}$. The acceleration in the vertical direction then increases to a peak (the peak reaction) denoted $Acc_{vert\_pr}$ at time $t_{pr}$. The peak reaction is followed by the lowest reaction which is a negative acceleration denoted $Acc_{vert\_1r}$ occurring at time $t_{1r}$. The end of the movement occurs at time $t_e$, with the acceleration denoted $Acc_{vert\_e}$.

Figure 4:
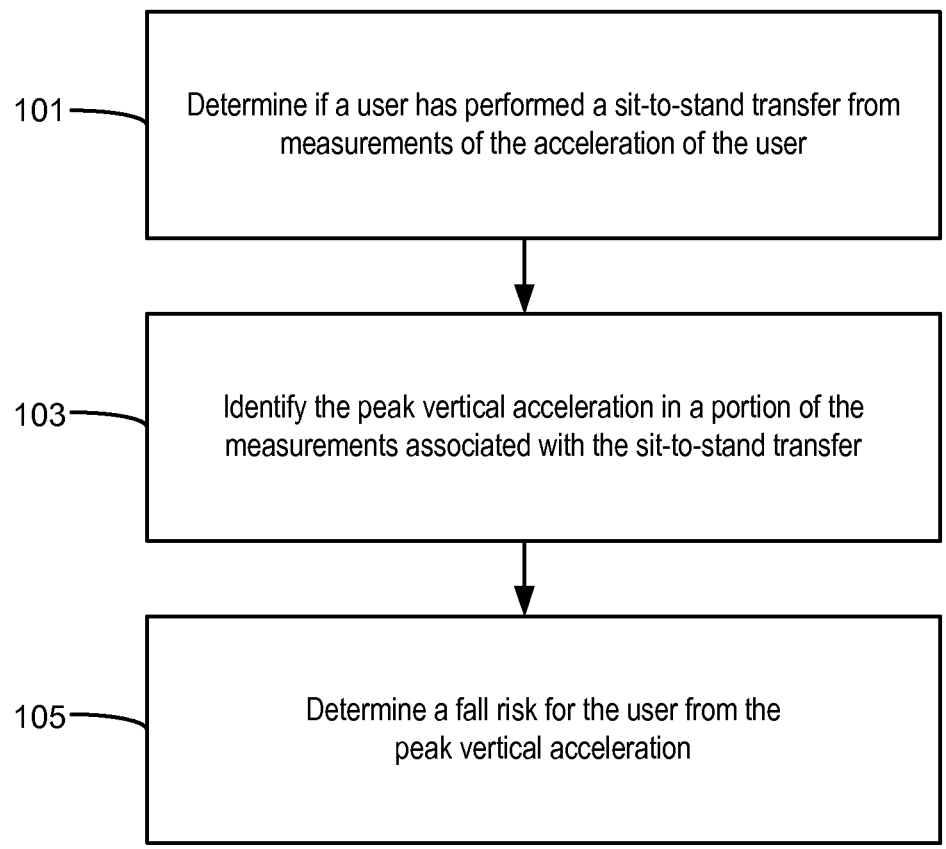
FIG. 4 is a flow chart illustrating a method of determining a fall risk according to an embodiment.

The flow chart in FIG. 4 illustrates a method of determining a fall risk for a user according to an embodiment. In step 101, it is determined whether the user has performed a sit-to-stand transfer. This step may be performed in a number of different ways, depending on the way in which the movements of the user are being monitored.

In some embodiments, the user may be performing a sit-to-stand transfer while located on a force plate that measures the forces generated by the user as they execute the transfer. In this case, step 101 may comprise receiving an indication (for example resulting from a button press) from a clinician who is observing the user while they perform the transfer or from the user when they perform a transfer, or it may comprise analyzing signals from an optical marker system or analyzing the forces measured by the force plate in order to determine if the user has performed a transfer.

In other embodiments, the user may be wearing or carrying a device that contains one or more movement sensors, such as an accelerometer, and the signals from this or these sensors can be processed to determine if the user has performed a transfer. In these embodiments, it may also be possible for the user to manually provide an indication that they have started and/or completed a transfer (for example by pressing a button on the device).

If it is determined that the user has performed a sit-to-stand transfer, the method then proceeds to identify the peak vertical acceleration generated by the user in completing the sit-to-stand transfer (step 103). This peak vertical acceleration will correspond generally to the peak labeled "peak reaction" in FIG. 3, and is the largest upward acceleration that occurs during the sit-to-stand transfer.

Where the movements of the user are being monitored using a force plate, a signal representing the vertical acceleration can be determined from the force measurements by dividing the measured forces by the mass of the user. Otherwise, where the movements of the user are monitored using an accelerometer, the acceleration in the vertical direction can be estimated from the signal from the three-dimensional accelerometer. In some embodiments, the vertical acceleration can be estimated as the norm of the three-dimensional acceleration measurements.

Thus, following the determination in step 101 that a sit-to-stand transfer has occurred (the determination also providing an indication of the time at which the transfer occurred, for example in terms of the start and end times of the transfer), a portion of the vertical acceleration signal around the identified sit-to-stand transfer is selected for analysis (i.e. the portion between the identified start and end times of the sit-to-stand transfer), and the peak vertical acceleration identified as the largest maximum in the portion of the vertical acceleration signal corresponding to the sit-to-stand transfer.

Figure 1:
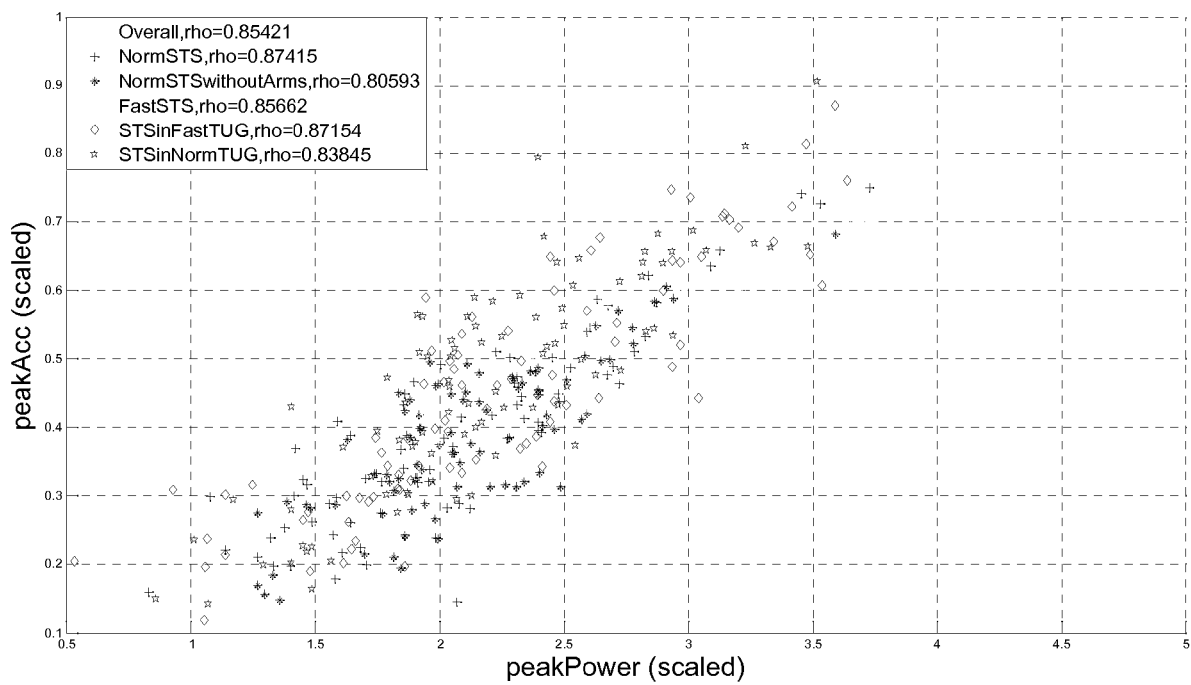
FIG. 1 is graph illustrating the correlation between peak vertical acceleration and peak power in a sit-to-stand transfer.
Figure 2:
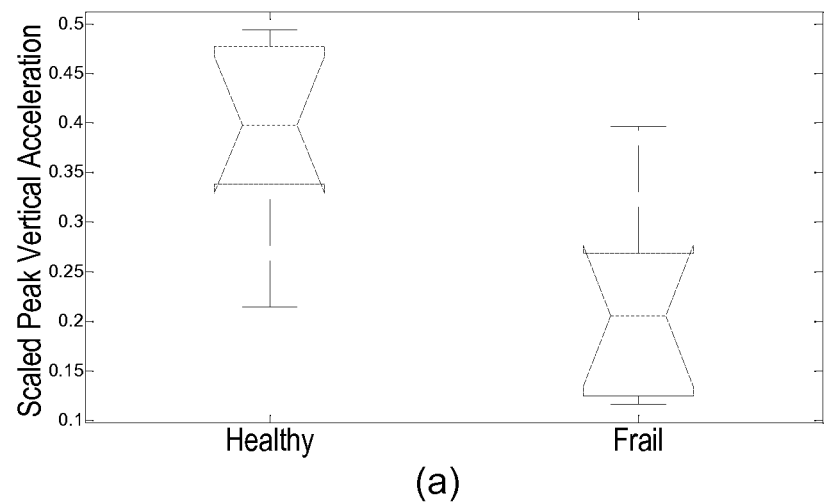
FIG. 2 illustrates the sensitivity of peak vertical acceleration and peak power to fall risk.
Figure 2:
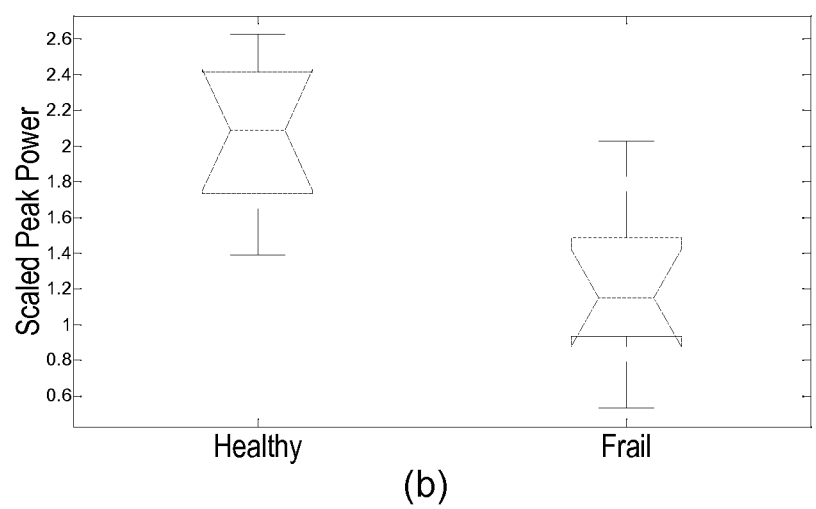

Once the peak vertical acceleration has been determined in step 103, the method proceeds to step 105 in which the peak vertical acceleration is used to estimate a fall risk for the user. In general, as shown in FIG. 2(a), those at a higher risk of falling produce lower peak vertical acceleration values than those at a lower risk of falling. Thus, in some embodiments, the fall risk can be inversely proportional to the peak vertical acceleration value (e.g. fall_risk $\alpha$ 1/peak_vertical_acceleration)

In some embodiments, a fall risk may be generated in step 105 from an average of the peak vertical acceleration generated by the user over a plurality of sit-to-stand transfers. The average of the peak vertical acceleration may be obtained from a number of sit-to-stand transfers performed in a single monitoring session or from sit-to-stand transfers performed over a number of different days.

In some embodiments, the fall risk determined in step 105 can be compared to previously-determined fall risks to identify a trend in the performance of the sit-to-stand transfer by the user. Thus, a decrease in the peak vertical acceleration (or average peak vertical acceleration) indicates an increase in the fall risk of the user, and vice versa.

In some embodiments, the number of times that the user performs a sit-to-stand transfer in a given time period (for example a day) can also be recorded and used in conjunction with the peak vertical acceleration to provide the indication of fall risk.

Using the peak vertical acceleration as the parameter for estimating fall risk has a number of advantages over the use of power or peak power. Firstly, the peak vertical acceleration is less sensitive to the accurate detection of the start and end points of the sit-to-stand transfer, which makes it more robust and reliable for fall risk assessment than power. In addition, the estimation of peak vertical acceleration requires less computational effort than estimating the power (which involves integration of acceleration signals). These advantages make the monitoring of peak vertical acceleration suitable for implementing long-term fall risk monitoring applications, for example using on-body sensors.

Figure 5:
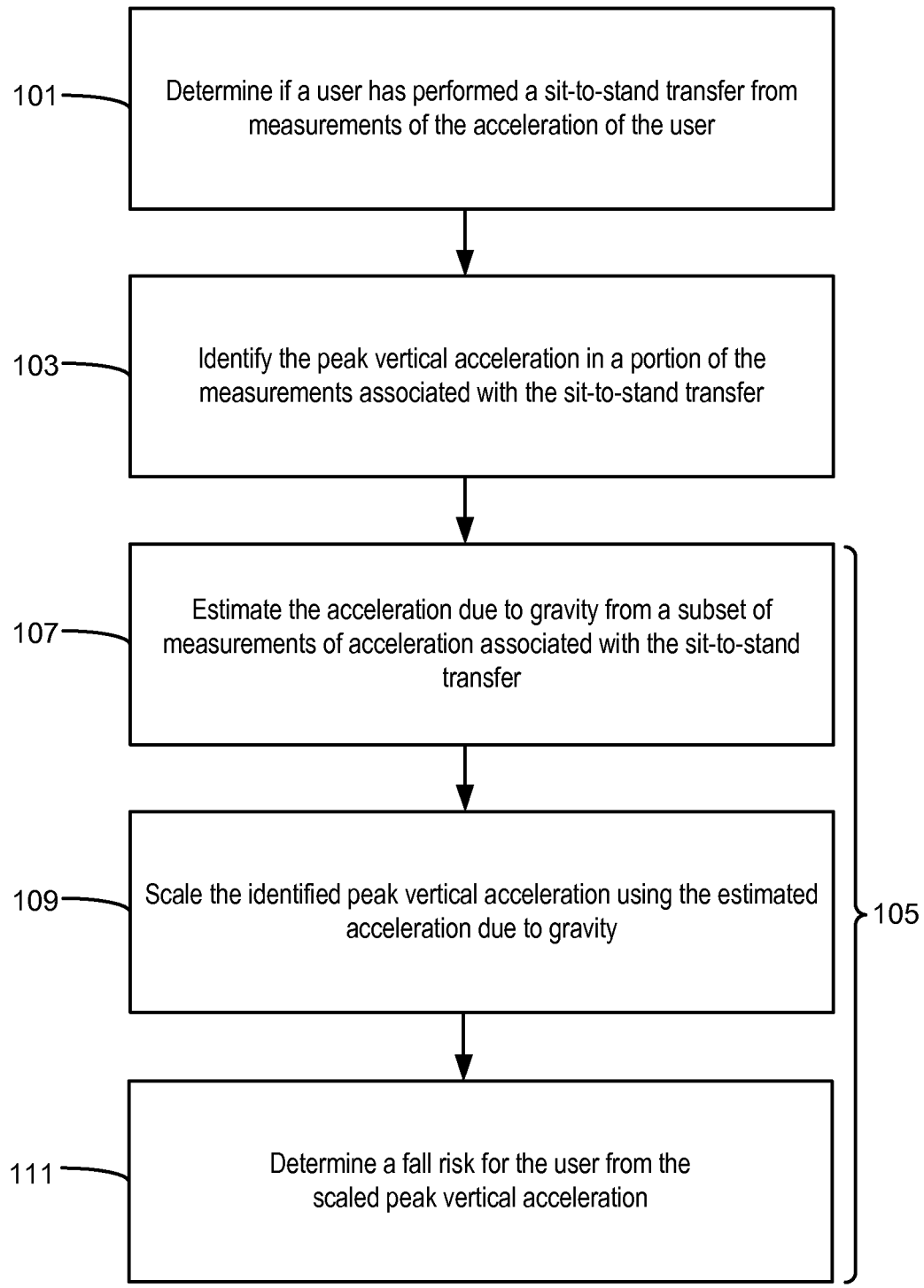
FIG. 5 is a flow chart illustrating a method of determining a fall risk according to an another embodiment.

A method of determining a fall risk according to another embodiment is shown in FIG. 5. In this method, the first two steps are the same as in FIG. 4. That is, it is determined if a user has performed a sit-to-stand transfer (step 101) and if so, the peak vertical acceleration during the transfer is identified (step 103).

In this embodiment, it is recognized that, particularly (but not exclusively) for on-body-sensor-based implementations of the invention, calibration errors in the sensor measurements can introduce errors into the assessment of fall risk.

Therefore, these calibration errors are accounted for by scaling the peak vertical acceleration using an estimate of gravitational acceleration that is derived from the measurements of vertical acceleration around the time that the sit-to-stand transfer is performed.

In particular, in step 107, an estimate of the acceleration due to gravity is estimated from the vertical acceleration signal, and in step 109 this estimate is used to scale the identified peak vertical acceleration to give a scaled peak vertical acceleration. The peak vertical acceleration is preferably scaled by subtracting the estimate of gravity from the peak vertical acceleration. The scaled peak vertical acceleration is then used to determine the fall risk for the user (step 111).

As the estimate of the gravitational acceleration is derived from the measurements of vertical acceleration from the sensor (e.g. accelerometer), the estimate will also be subject to the sensor calibration error, and scaling the peak vertical acceleration with this estimate will largely remove the calibration error.

It will be appreciated that steps 101, 103, 107 and 109 do not have to be performed in the order shown in FIG. 5. For example, it is possible to determine and periodically update an estimate of the acceleration due to gravity for use when a sit-to-stand transfer is subsequently detected, and then apply this to a peak vertical acceleration when this is identified in step 103. Alternatively, the estimate of gravity can be used to scale all of the vertical acceleration measurements, with the peak vertical acceleration being identified from the scaled vertical acceleration measurements.

In some embodiments, the estimate of acceleration due to gravity is derived in step 107 by taking the average (e.g.) mean value of the vertical acceleration over a plurality of vertical acceleration samples in a predetermined period prior to the indicated start of the sit-to-stand transfer. The predetermined period should generally correspond to a period of time in which the user is sitting on the chair, and therefore the vertical acceleration should be dominated by acceleration due to gravity. The predetermined period can be any suitable length, for example, 3 seconds.

In some embodiments, it can be confirmed that the vertical acceleration in the predetermined period likely results from gravity only by determining if the standard deviation of the vertical acceleration in the predetermined period is lower than a threshold. In some embodiments, the threshold can be 0.1, but it will be appreciated that other values can be used. It will also be appreciated that measures other than the standard deviation can be used to determine if the vertical acceleration in the predetermined period likely result from gravity only, such as the variance of the vertical acceleration or the range. If it is lower than the threshold, the average of the vertical acceleration values can be determined and used as the estimate of acceleration due to gravity. In the example of FIG. 3, the average value of the vertical acceleration from sample index 100 to 250 (where the sit-to-stand transfer starts) is used as the estimate of acceleration due to gravity for scaling the peak vertical acceleration of the transfer.

In embodiments where an estimate of the acceleration due to gravity is determined and periodically updated, the acceleration measurements can be continuously or regularly monitored for the occurrence of a predetermined period as described above (i.e. where the standard deviation is below the threshold), and if such a period occurs, a new value for the estimate of gravitational acceleration can be determined using the samples in that period.

Figure 6:
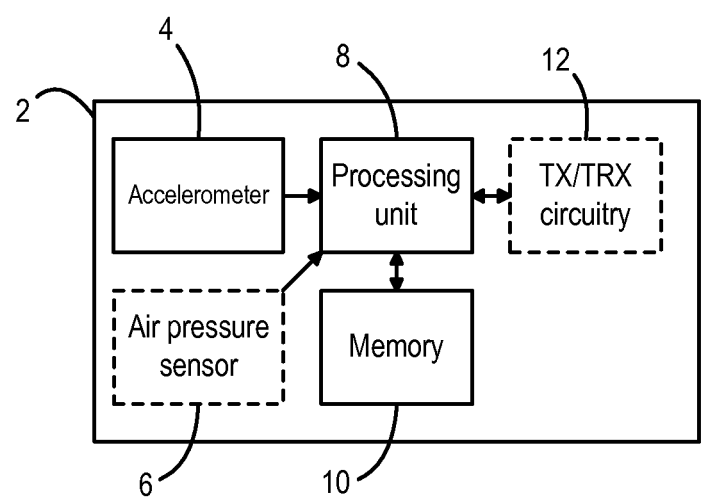
FIG. 6 is a block diagram of an apparatus according to an embodiment of the invention.

FIG. 6 illustrates an apparatus 2 for use in determining a fall risk for a user according to an embodiment of the invention. In this embodiment, the invention provides an apparatus in the form of a sensor unit 2 that is to be worn by a user. The sensor unit 2 can be provided in the form of a pendant with a neck cord for placement around the user's neck. Alternatively, the sensor unit 2 can be configured to be worn at or on a different part of the user's body, such as the trunk, pelvis or sternum, and will comprise a suitable arrangement for attaching the sensor unit 2 to that part of the body (for example a belt or a strap if the unit 2 is attached to the pelvis or sternum).

The sensor unit 2 is used to measure the movement of the user and can be used to process the measurements to determine when the user has executed a change in posture from a sitting posture to a standing posture and the peak vertical acceleration that occurs during this movement. The sensor unit 2 can also be used to determine the fall risk for the user 4 from the determined peak vertical acceleration.

In alternative implementations, some or all of the processing of the measurements, determination of the peak vertical acceleration and the indication of the fall risk can be performed in a base unit that is separate to the sensor unit 2 worn by the user (not shown in FIG. 6). In this case, the sensor unit 2 can transmit the movement measurements or information on the identified transfers to the base unit using a wired or wireless connection.

In the illustrated embodiment, the sensor unit 2 comprises an accelerometer 4 that measures acceleration along three orthogonal axes (and that outputs respective signals indicating the acceleration along each of the axes) and an optional sensor 6 that measures the altitude or height of the sensor unit 2 above the ground (or more particularly that measures changes in the altitude or height of the sensor unit 2 above the ground, or enables those changes to be measured). The sensor 6 for measuring the altitude or height of the sensor unit 2 can comprise, for example, an altimeter or air pressure sensor, although those skilled in the art will be aware of other types of sensors that can be used. In some embodiments, the measurements from the accelerometer 4 can be processed to determine the height of the sensor unit 2 above the ground, or to determine the change in height of the sensor unit 2. The signals output by the accelerometer 4 and sensor 6 (where present) are provided to a processing unit 8 for analysis.

The sensor unit 2 also comprises a memory 10 and optionally also a transmitter or transceiver circuitry 12. The memory 10 is used for storing measurements from the accelerometer 4 and sensor 6, and for storing the results of the analysis by the processor 8. The transmitter or transceiver circuitry 12 can be used for transmitting the measurements or the results of the analysis to a remote (base) unit or a computer where they can be viewed or studied by the user or a healthcare provider.

In some embodiments, the accelerometer 4 is a microelectromechanical system (MEMS) accelerometer. The acceleration experienced by the accelerometer 4 can be sampled at a rate of 50 Hz, although it will be appreciated that many other sampling frequencies can be used. Where sensor 6 is an air pressure sensor or altimeter, the measurements of the height of the sensor unit 2 above the ground can be sampled at a frequency of around 1.8 Hz, although again it will be appreciated that other sampling frequencies can be used.

Depending on the particular type of sensor used for the sensor 6 for measuring height, the sensor 6 may output signals indicative of the height above the ground (or sea level in the case of an air pressure sensor), in which case the time series of height measurements can be analyzed by the processing unit 8 to determine the change in height from one measurement sample to the next (or over a predetermined number of measurement samples). Alternatively, the sensor 6 can directly output an indication of the change in height of the sensor unit 2 from the previous or an earlier specified measurement sample.

As noted above, in some embodiments, the measurements collected by the accelerometer 4 and sensor 6 can be analyzed by the processing unit 8 in the sensor device 2 to determine when a user has performed a sit-to-stand transfer, the peak vertical acceleration experienced by the user when executing the sit-to-stand transfer, and a fall risk for the user from the peak vertical acceleration. Alternatively, the measurements from the accelerometer 4 and sensor 6 could be transmitted to a base unit via the transmitter/transceiver circuitry 12, with the base unit analyzing the measurements to determine the occurrence of sit-to-stand transfer. In either case, the processing can be performed in (near) real-time or the measurements from the accelerometer 4 and the sensor 6 can be stored in the memory 10 or the base unit for future processing (i.e. offline).

It will be appreciated that in alternative implementations of the invention, rather than being provided in the form of an on-body device that comprises an accelerometer 4 and sensor 6, the apparatus 2 may be configured to use or include a force plate to measure the vertical forces exerted by the user when performing the sit-to-stand transfer. In that case, the processing unit 8 can be configured to process the force plate measurements and determine the vertical acceleration of the user in the sit-to-stand transfer.

Detection of a Sit-to-Stand Transfer in Measurements of Acceleration

An exemplary algorithm for processing accelerometer measurements to detect a sit-to-stand transfer is described below with reference to FIGS. 7, 8 and 9. This technique has been described in International patent application no. PCT/IB2012/053083 which was filed on 19 Jun. 2012 in the name of Koninklijke Philips Electronics N.V., the content of which is hereby incorporated by reference. It will be appreciated by those skilled in the art that the invention is not limited to the use of the technique described below for detecting sit-to-stand transfers, and other techniques for detecting a sit-to-stand transfer could be used.

Figure 7:
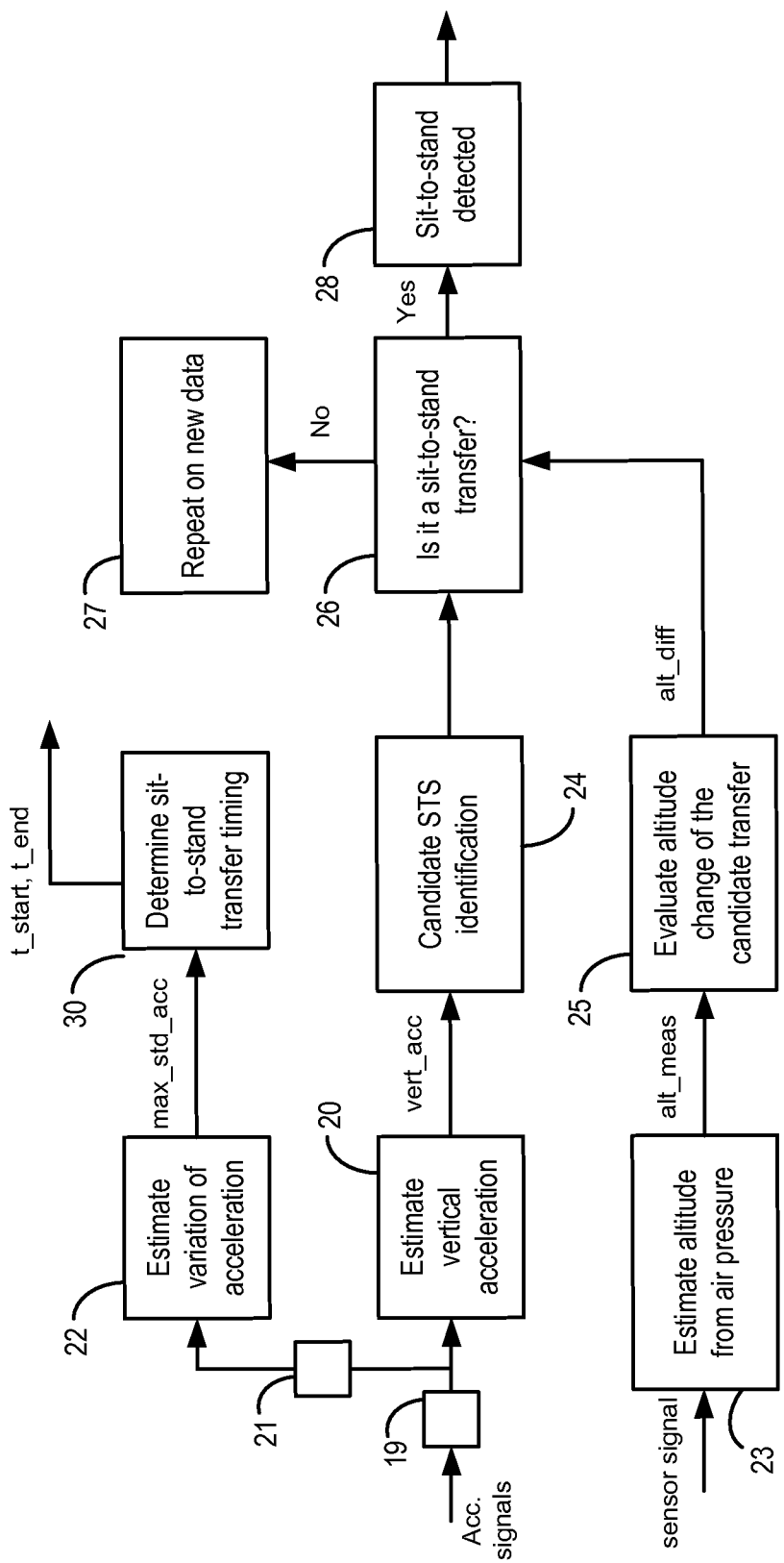
FIG. 7 is a block diagram illustrating an algorithm for detecting a sit-to-stand transfer in measurements of the vertical acceleration of the user.

FIG. 7 shows an exemplary algorithm for detecting a sit-to-stand transfer and for determining the timing of the transfer. The algorithm takes as an input the three-dimensional acceleration signal measured by the accelerometer 4 (which comprises a separate signal for each of the three axes of the accelerometer 4) and an air pressure measurement from air pressure sensor 6.

The initial part of the algorithm, represented by blocks 19, 20, 21, 22 and 23, is a pre-processing stage in which the accelerometer and pressure sensor signals are processed for use in the subsequent analysis stages of the algorithm. Firstly, the 3D acceleration signals from the accelerometer 4 are low-pass filtered (block 19) to remove noise which could affect the accuracy of the subsequent processing. In one embodiment, a Butterworth low-pass filter with a cut-off frequency of 2 Hz is applied to the signals from each of the three axes of the accelerometer 4. Alternatively, it would be possible to apply different filter characteristics such as a Chebyshev low-pass filter or other types of filter known to those skilled in the art. It will also be appreciated that the cut-off frequency of 2 Hz could be varied dependent on the particular characteristics of the noise from the accelerometer 4.

As the orientation of the sensor unit 2 relative to the fixed reference frame (such as the Earth) in which the user moves can change (particularly where the sensor unit 2 is in the form of a pendant), it is necessary to process the measurements from the accelerometer 4 to determine the vertical component of acceleration experienced by the sensor unit 2 (and therefore user) during the movement.

Therefore, the low-pass filtered 3D acceleration signals are input to block 20 that estimates the vertical acceleration. The vertical acceleration is denoted vert_acc.

One technique for estimating the vertical component of acceleration from a 3D accelerometer signal having an arbitrary orientation is described in WO 2010/035191, the content of which is hereby incorporated by reference. Briefly, according to that technique, the vertical component of acceleration is estimated from measurements of acceleration acting on an accelerometer, the accelerometer having an arbitrary orientation relative to the fixed reference frame, by (i) examining the signals from the accelerometer to identify the axis of the accelerometer having the highest component of acceleration, (ii) determining the orientation of the accelerometer by determining the angle between the acceleration acting on the accelerometer (this acceleration being assumed to be generally due to gravity) and the axis with the highest component of acceleration and (iii) using the estimated orientation of the accelerometer to determine the acceleration in the vertical direction from the measurements of acceleration.

Those skilled in the art will be aware of other techniques for estimating the vertical component of acceleration from the measurements from a 3D accelerometer. For example, the sensor unit 2 can include a gyroscope for providing a signal indicating the orientation of the sensor unit 2, and this signal can be used to derive the vertical component of acceleration.

Figure 8:
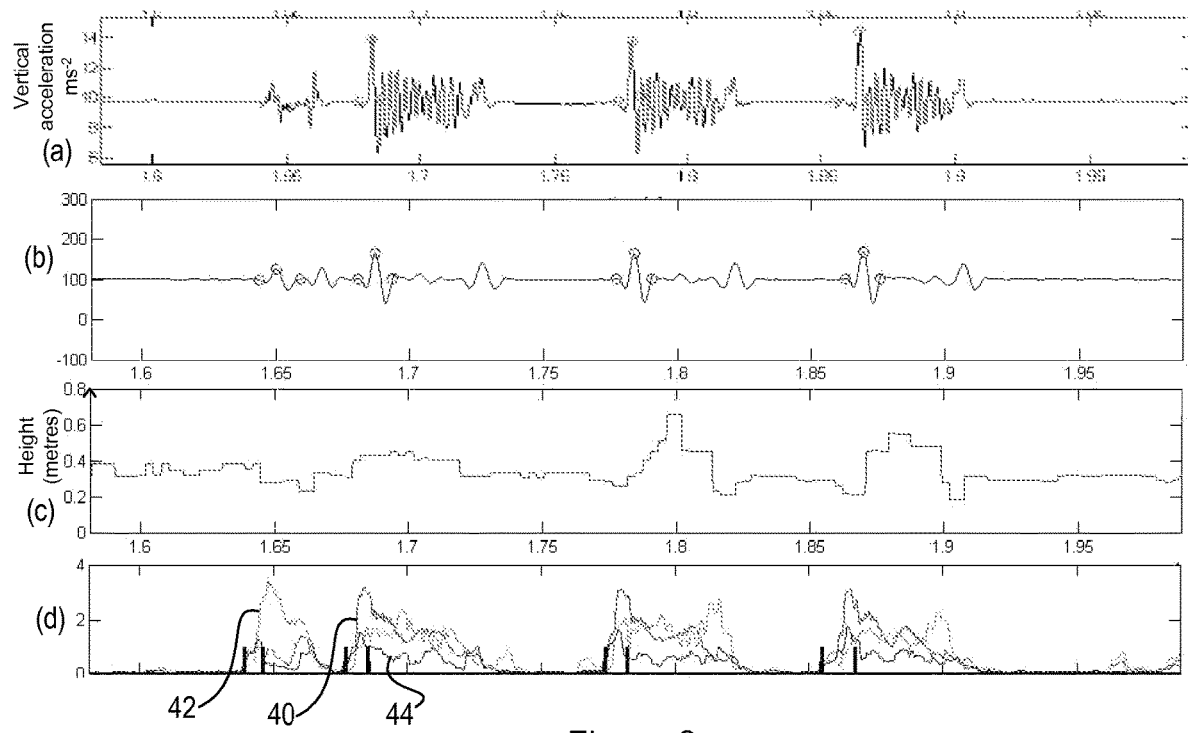
FIG. 8 shows the input signals to the algorithm and the signals obtained during some of the processing steps.

FIG. 8(*a*) shows an exemplary signal representing the vertical acceleration obtained from measurements by a sensor unit 2 of a user performing a sit-to-stand transfer, walking for 3 meters and then sitting back down, which was repeated three times. It can be seen in FIG. 8(*a*) that there are three separate areas of activity represented in the signal.

Another stage of the pre-processing concerns the calculation of an estimate of the variation of acceleration. Firstly, a high pass filter 21 is applied to each of the low-pass filtered 3D acceleration signals in order to remove the DC component. In one embodiment, a Butterworth high-pass filter with a cut-off frequency of 0.5 Hz is used to remove the D.C. component in the acceleration signals. It will be appreciated that another filter, for example a Chebyshev high-pass filter or other types of filter known to those skilled in the art could be used. It will also be appreciated that a different cut-off frequency to 0.5 Hz could be chosen.

After high-pass filtering, the variation of the acceleration is estimated in block 22. In a preferred embodiment, the standard deviation of each of the three components of the 3D acceleration signal is computed for a time t over a window of predetermined length (for example, one second, although it will be appreciated that another appropriately sized window could be used) and the maximum standard deviation out of the three axes is identified. The maximum standard deviation at time t is denoted max_std_acc and is given by equation 1 below.

$$\text{max\_std\_acc} = \max[\text{std}(\text{acc}\_i(t-0.5, t+0.5)), i=x,y,z] \quad (1)$$

FIG. 8(d) shows the standard deviation calculated for each of the three axes of acceleration. In FIG. 8(d), line 40 corresponds to the x-axis accelerometer signal, line 42 corresponds to the y-axis accelerometer signal, and line 44 corresponds to the z-axis accelerometer signal.

A third pre-processing stage 23 estimates the altitude of the sensor unit 2 from the measurements from the air pressure sensor 6. As indicated above, the input to this stage 23 is the raw air pressure signal $p_t$ from the air pressure sensor 6. As mentioned previously, the air pressure can be sampled at a rate of 1.8 Hz (or in any case at a much lower sampling rate than the acceleration signals). Therefore, the air pressure signal $p_t$ is firstly upsampled to match the sampling rate (e.g. 50 Hz) of the acceleration signals (the upsampled pressure signal is denoted $p_t'$). The altitude at time t (denoted alt_t) can then be estimated from the air pressure sensor measurements using equation 2 below:

$$\text{alt}\_t = 44330 * (1 - p_t'/101325)^{0.19} \quad (2)$$

Equation (2) is derived from the air pressure to altitude conversion function shown in equation (3):

$$\text{alt}\_t = \frac{T_0}{L}\left(1 - \left(\frac{p}{p_0}\right)^{\frac{RL}{gM}}\right) \quad (3)$$

Where:

| Symbol | Quantity | Typical Value |
|---|---|---|
| alt_t | Altitude in meters | |
| p | Air pressure | |
| $p_0$ | Standard atmospheric pressure at sea level | 101325 kPa |
| L | Temperature lapse rate | 0.0065 Km$^{-1}$ |
| $T_0$ | Standard temperature at sea level | 288.15 K |
| g | Gravitational acceleration at Earth's surface | 9.80665 ms$^{-2}$ |
| M | Molar mass of dry air | 0.0289644 kg mol$^{-1}$ |
| R | Universal gas constant | 8.31447 J mol$^{-1}$ K$^{-1}$ |

The resulting altitude signal is then smoothed, preferably with a median filter having a predetermined length, for example of around 3 seconds. The filter is applied to the time series of estimated altitudes, resulting in a smoothed altitude signal alt_meas which is output from the altitude estimation stage 23, as shown in FIG. 8(c). In FIG. 8(c), the y-axis represents altitude in meters relative to sea level.

It will be appreciated that in alternative embodiments of the invention where a different type of altitude, height or change in height sensor is used, processing stage 23 may be adapted or omitted as appropriate.

Following the pre-processing of the input signals, various features are extracted in order to determine if a sit-to-stand transfer has occurred, and if so, the power of the user in performing the sit-to-stand transfer.

Two main stages of feature extraction are required in order to determine if a sit-to-stand transfer has occurred. The first stage 24 identifies the candidate movements in the vert_acc signal. In particular, block 24 matches the vert_acc signal to a predetermined pattern representing the vertical acceleration that is expected to occur during a sit-to-stand transfer.

In some implementations, the first stage 24 of the feature extraction applies a matched filter having an impulse response that approximates the vertical acceleration experienced during a sit-to-stand transfer to the vertical acceleration signal (vert_acc) output from the vertical acceleration estimation block 20. The output of the matched filter is a set of coefficients that indicate the match of the measurements to the pattern. Each coefficient represents the match of a number of consecutive measurement samples (covering a time period of the same length as the predetermined pattern) to the predetermined pattern. The higher the coefficient, the better the match of the measurements to the pattern (and therefore the greater the chance that a sit-to-stand transfer has occurred). The filtered signal is denoted vert_acc_matfilt and is shown in FIG. 8(b).

Figure 9:
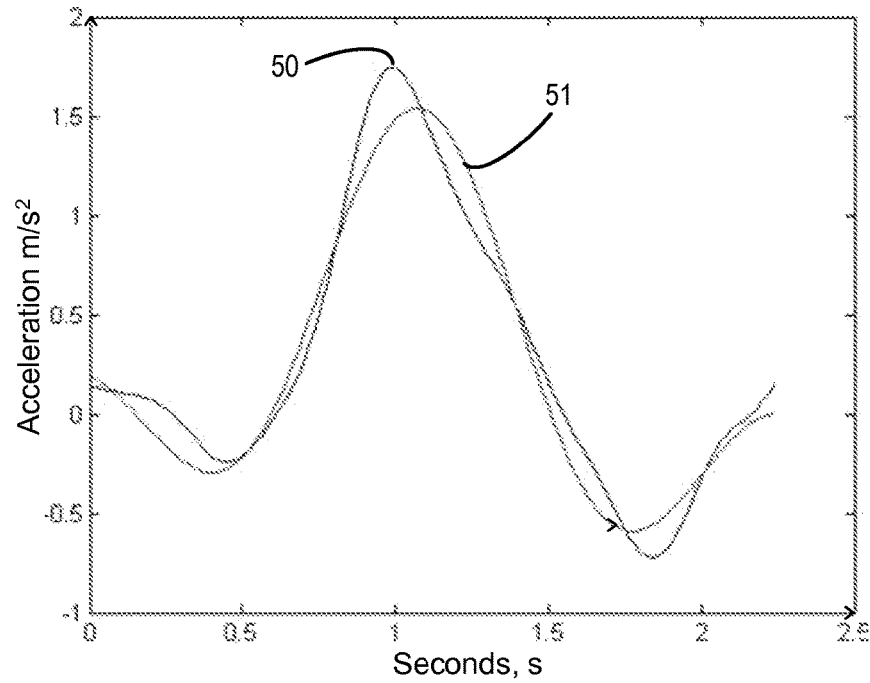
FIG. 9 illustrates an exemplary matched filter which has been optimized for use in detecting a sit-to-stand transfer.

In some implementations, the matched filter used in block 24 can be as shown in FIG. 9, which has been optimized to detect a sit-to-stand transfer. The matched filter shown in FIG. 9 excludes gravity (9.8 ms$^{-2}$) The first curve 50 shows a typical vertical acceleration pattern of a sit-to-stand transfer. The second curve 51 shows an applied matched filter characteristic that approximates the first curve 50. It will be appreciated that the matched filter characteristic may be expressed using many different functions, but in this implementation, the matched filter characteristic is given by equation 4 below.

$$A_1 \cdot \text{sinc}[W_1(t-t_1)] + A_2 \cdot \text{sinc}[W_2(t-t_2)] \quad (4)$$

This characteristic is a combination of two sinc functions with scale parameters defined in p. p is a parameter vector with six elements:

$$[A_1, A_2, W_1, W_2, t_1, t_2] \quad (5)$$

Each entry in p defines a different scale parameter. $A_1$ and $A_2$ are amplitude scale parameters, which define the peak deviation of the two sinc waves respectively. The parameters $W_1$ and $W_2$ are frequency scale parameters, which define the frequency of the two sinc waves. The parameters $t_1$ and $t_2$ are phase scale parameters, which define the position of the sinc waves. The values of the six elements in the parameter vector p are set to tune the function of the matched filter to the sit-to-stand transfer characteristic 50 in FIG. 7.

It will be appreciated that the values of the elements of the parameter vector p can be provided by many known curve-fitting methods. In one case, the desired parameters could be calculated by applying a nonlinear least-squares regression algorithm, however many other types of fitting algorithms are well known in the art and could be applied. The nonlinear least-squares regression algorithm generates different parameter combinations corresponding to different functions. The generated functions are then fitted to the data set of desired patterns according to a least-squared error criterion. When the function yields a minimum value of least square error among the combination of parameters, an optimized fit has been found.

After matched filtering, the filtered signal is processed to identify movements that may correspond to a sit-to-stand transfer by the user. The processing consists of firstly identifying any peak having a magnitude in a predetermined range in the vert_acc_matfilt signal. In the exemplary signal shown in FIG. 8(d), peaks whose magnitudes are in the range of 110 to 200 are identified. It will be appreciated that this part of the processing can alternatively comprise identifying any peak having a magnitude above a threshold value in the vert_acc_matfilt signal. In this case, the threshold can correspond to the lower bound for the predetermined range described above. However, this classification may result in a higher false positive identification rate than the range implementation described above.

For each identified peak, the algorithm attempts to identify respective local minima occurring within a predetermined time period before and after the identified peak in the vert_acc_matfilt signal. In the exemplary signal shown in FIG. 8(b), the algorithm looks for local minima within a period of 2 seconds before and after the identified peak. If no local minima are identified for a particular peak, that peak of the vert_acc_matfilt signal is not considered to correspond to a sit-to-stand transfer.

Finally, a candidate movement corresponding to a sit-to-stand transfer is identified as a peak having the required local minima and at which the difference between the magnitude of the peak and the magnitude of the local minimum before the peak is less than a first threshold value, the difference between the magnitude of the peak and the local minimum after the peak is less than a second threshold value, and the magnitude of the local minimum after the peak is less than the magnitude of the local minimum before the peak.

In simplified implementations, the magnitude requirements applied to the local minima can be relaxed, with the algorithm simply identifying the peak, the magnitude of the peak, and the presence of local minima before and after the peak.

In the exemplary signal shown in FIG. 8(b), the first threshold is 25 and the second threshold is 200. It will be appreciated that the values chosen for the first and second thresholds are tuned to an experimental dataset, and different threshold values could be used.

It can be seen in FIG. 8(b) that four possible movements have been highlighted as candidate sit-to-stand transfers, occurring roughly at times 1.65, 1.69, 1.78 and 1.87.

Candidate sit-to-stand transfers are identified as actual sit-to-stand transfers when they occur at the same time as a change in the height of the sensor unit 2 that is within a predetermined range. Thus, block 25 determines the change in height or altitude that has occurred during each candidate sit-to-stand transfer. In order for block 25 to evaluate the altitude change of a candidate sit-to-stand transfer identified in the matched filtering block 24, block 25 receives a copy of the vert_acc_matfilt signal and indications of which parts of the signal correspond to candidate sit-to-stand transfers from the matched filtering block 24. Block 25 also receives the estimated altitude measurement signal, alt_meas, from estimation block 23.

A candidate sit-to-stand transfer found in the output from the matched filter 24 consists of three key samples. These are the peak, the local minimum before the peak (min_1), and the local minimum after the peak (min_2). These samples are marked for one of the candidate sit-to-stand transfers in FIG. 8(b). In order to estimate the altitude change over the correct time period, it is necessary to identify the right samples in the altitude measurement signal.

Firstly, the nearest sample (s1) before the local minimum before the peak (min_1) whose value is larger than a threshold is found. Secondly, the nearest sample (s2) after the local minimum after the peak (min_2) whose value is larger than a threshold is found. It will be appreciated that theoretically, this threshold should be $g^2$; however in practice, different values might be provided by the training dataset due to slight inaccuracies in the accelerometer, for example. In one implementation, this threshold is 98.

The altitude change of the candidate sit-to-stand transfer is then estimated as the difference between the altitudes at samples s1 and s2.

Since there may be small fluctuations in the altitude measurement (due to noise), the altitude change of the candidate sit-to-stand transfer can be estimated as the difference between the mean of the altitude measurement over a time window starting at the second local minimum, and the mean of the altitude measurement over a time window ending at the first local minimum. These time windows can be one second, although it will be appreciated that windows of other lengths can be used. In equation form, this can be expressed as $$\text{alt\_diff} = \text{mean}(\text{alt\_meas}(s2:s2+t_w)) - \text{mean}(\text{alt\_meas}(s1-t_w:s1)) \quad (6)$$

where $t_w$ is the length of the window. In this way, the mean value of the altitude data one second before the start and one second after the candidate transfer is evaluated. When a sit-to-stand transfer has occurred, a lower altitude should be observed before the transfer (when the user is in the sitting position) than the altitude observed after the transfer (when the user is in the standing position).

The output of the candidate sit-to-stand transfer identification block 24 and the altitude change block 25 are provided to a decision block 26 which determines whether any of the candidates are sit-to-stand transfers. In particular, any candidate movement occurring at the same time a change in altitude or height within a predetermined range is deemed to be a sit-to-stand transfer. The change in height should be an increase in height (by definition of a sit-to-stand transfer), and the predetermined range can be, for example, between 0.1 and 0.75 meters. In some cases the upper bound can be omitted at the expense of a greater false positive detection rate.

It can be seen in FIG. 8 that of the four candidate movements highlighted in FIG. 8(b), the last three occur at the same time as an increase in height that is in the range 0.1 to 0.75. Thus, the candidate movements at times 1.69, 1.78 and 1.87 are deemed to correspond to sit-to-stand transfers. The candidate movement at time 1.65 coincides with a reduction in the measured height and is therefore discarded. The algorithm then repeats for a new set of input data (represented by block 27 in FIG. 7).

As described above, step 103 of identifying the peak vertical acceleration makes use of estimated timing information of detected sit-to-stand transfers (for example estimated start and end times) for detected sit-to-stand transfers.

Therefore, a block 30 determines the timing of the sit-to-stand transfer and receives inputs from the block 22 which estimates the variation of the acceleration and the vertical acceleration profile after matched filtering, vert_acc_matfilt.

In a simple embodiment, s1 and s2 are used to identify the start and end of the sit-to-stand transfer for the purposes of identifying the peak vertical acceleration.

However, as will be known to those skilled in the art, the matched filter introduces a delay which is related to the number of filter taps. This delay causes the candidate sit-to-stand transfer to be delayed with respect to the actual onset of the sit-to-stand transfer in the vert_acc_matfilt signal. Therefore, in some implementations, the output of block 22 that estimates the variation in acceleration, max_std_acc can be used to determine the actual onset of a sit-to-stand transfer.

Firstly, the most adjacent sample in the signal max_std_acc before s1 whose value is smaller than a threshold is identified. This threshold determines where the onset of the actual sit-to-stand transfer (denoted t_start) is found. In an exemplary case the threshold may be 0.35, but it will be understood that different threshold values smaller than 1 may be used, with the specific value being selected, in part, based on the size of the computing window being applied to the signal. Then, the largest local minimum of the estimate of the vertical acceleration (vert_acc) between s1 and s2 (in other words, the lowest value of vert_acc between s1 and s2) is found. The most adjacent sample after the largest local minimum of the estimate of the vertical acceleration, whose value is larger than a threshold value, which in a particular implementation is based on gravity (i.e. 9.8 ms$^{-2}$), is defined as the end of the actual sit-to-stand transfer (t_end). The solid black bars in FIG. 8(b) and corresponding circles in FIG. 8(a) indicate t_start and t_end for each actual sit-to-stand transfer. The values for t_start and t_end for each detected sit-to-stand transfer are output by block 30 and used to determine the subset of samples that are analyzed to determine the peak vertical acceleration.

There is therefore provided a method and apparatus that can estimate a fall risk for a user through analysis of a sit-to-stand transfer, and in particular through the estimation of the peak vertical acceleration generated by the user in performing a sit-to-stand transfer.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A non-transitory computer program product, comprising computer program code that, when executed on a computer or processor, causes the computer or processor to determine a fall risk for a user by:
   low-pass filtering a plurality of measurements of an acceleration which were measured by an accelerometer of a device of the user, wherein the plurality of measurements include a separate accelerometer signal for each of three axes of the accelerometer, to generate three low-pass filtered accelerometer signals, including a separate low-pass filtered accelerometer signal for each of the three axes;
   processing the three low-pass filtered accelerometer signals to determine a vertical component of acceleration;
   high-pass filtering the three low-pass filtered accelerometer signals to generate a separate band-pass filtered accelerometer signal for each of the three axes;
   computing three standard deviations, one for each of the three band-pass filtered accelerometer signals, for a time window of a predetermined length;
   identifying a maximum standard deviation of the three standard deviations;
   estimating a change in altitude of the device from an air pressure measured by a sensor of the device;
   analyzing the plurality of measurements of the acceleration of the user to determine if the user has performed a sit-to-stand transfer by:
   identifying a sub-portion of the vertical component of acceleration as a candidate sit-to-stand movement; and
   identifying the sub-portion as including an actual sit-to-stand transfer in response to the candidate sit-to-stand movement occurring during a same predetermined time window as a change in altitude of the sensor;
   determining a timing of the sit-to-stand transfer in the sub-portion based on the maximum standard deviation, including a start time and an end time of the sit-to-stand transfer;
   identifying a peak vertical acceleration of the user during the sit-to-stand transfer from the plurality of measurements of the acceleration of the user from samples of the sub-portion corresponding to the timing, wherein the identified peak vertical acceleration is scaled using an estimate of gravity obtained from the measurements of the acceleration of the user thereby producing a scaled peak vertical acceleration; and
   estimating a fall risk for the user from the scaled peak vertical acceleration, wherein the fall risk is inversely proportional to the scaled peak vertical acceleration.

2. An apparatus for estimating a fall risk for a user, the apparatus comprising:
   an accelerometer configured to take a plurality of measurements of acceleration of the user and generate three acceleration signals respectively indicative of an acceleration along each axis of three orthogonal axes;
   a low-pass filter configured to low pass filter each of the three acceleration signals, generating three low-pass filtered acceleration signals;
   a high-pass filter configured to high pass filter each of the three low-pass filtered acceleration signals, generating three band-pass filtered acceleration signals;
   a computer processor configured to:
   compute a standard deviation of each of the three band-pass filtered acceleration signals based on samples for a time window of a predetermined length, generating three standard deviation signals respectively for the three band-pass filtered acceleration signals;
   analyze the plurality of measurements of the acceleration of the user to determine if the user has performed a sit-to-stand transfer by matching a vertical acceleration signal of the three band-pass filtered acceleration signals with a predetermined pattern representing a vertical acceleration that is expected to occur during the sit-to-stand transfer where a matched filter applies an impulse response that is an approximated vertical acceleration experienced during the sit-to-stand transfer to the vertical acceleration signal;

determine a timing of the sit-to-stand transfer based on a maximum standard deviation of the three standard deviation signals;

identify a peak vertical acceleration of the user during the sit-to-stand transfer from the plurality of measurements of the acceleration of the user based on the determined timing, wherein the identified peak vertical acceleration is scaled using an estimate of gravity obtained from the plurality of measurements of the acceleration of the user thereby producing a scaled peak vertical acceleration; and estimate a fall risk for the user by computing an inverse of the scaled peak vertical acceleration.

3. A device that is configured to be worn by a user, the device comprising:
the apparatus as claimed in claim 2.

4. A system, comprising:
a device that is configured to be worn by a user, the device comprising the accelerometer as claimed in claim 2; and
a base unit that is configured to communicate with the device, and the base unit comprising the computer processor as claimed in claim 2.

5. A system, comprising:
a force plate; and
a base unit that comprises the apparatus as claimed in claim 2, wherein the computer processor is configured to receive measurements of forces from the force plate and to process the plurality of measurements of forces to determine measurements of the acceleration.

6. The apparatus of claim 2, wherein the computer processor is configured to:
identify a signal of the three low-pass filtered acceleration signals having a highest component of acceleration;
determine an orientation of the accelerometer by determining an angle between an acceleration acting on the accelerometer and an axis for the signal with the highest component of acceleration; and
determine a vertical component from the plurality of measurements of acceleration based on the orientation of the accelerometer.

7. The apparatus of claim 6, wherein the acceleration acting on the accelerometer is an acceleration due to gravity.

8. The apparatus of claim 6, wherein the computer processor is configured to determine the timing by:
identifying a first sample in the vertical component with a first value smaller than a first predetermined threshold to determine an onset of the sit-to-stand transfer; and
identifying a second sample after a largest local minimum of the vertical component with a second value greater than a second predetermined threshold to determine an end of the sit-to-stand transfer,
wherein the peak vertical acceleration is identified based on the onset and the end of the sit-to-stand transfer.

9. The apparatus of claim 8, wherein the onset and the end of the sit-to-stand transfer are utilized to determine a subset of samples that are analyzed to determine the peak vertical acceleration.

10. The apparatus of claim 8, further comprising:
a sensor configured to measure an altitude or a height of the apparatus above ground.

11. The apparatus of claim 10, where the sensor is one of an altimeter or air pressure sensor.

12. The apparatus of claim 10, where the computer processor determines the sit-to-stand transfer is a true sit-to-stand transfer when the sit-to-stand transfer occurs at a same time as a change in the height of the sensor within a predetermined range.

13. The apparatus of claim 12, where the peak vertical acceleration is determined during the sit-to-stand transfer only if the sit-to-stand transfer is a true sit-to-stand transfer.

14. The apparatus of claim 13, where the peak vertical acceleration is discarded in response to the sit-to-stand transfer not being a true sit-to-stand transfer.

15. The apparatus of claim 2, wherein an output of the matched filter is a set of coefficients that indicate a match to the predetermined pattern.

16. The apparatus of claim 15, wherein each coefficient of the set of coefficients represents a match of a number of consecutive measurement samples covering a time period of a same length as the predetermined pattern.

17. The apparatus of claim 2, wherein the gravity is obtained from the plurality of measurements of acceleration in a time period before a start of the sit-to-stand transfer only if the three standard deviation signals are less than a threshold value.

18. The apparatus of claim 2, wherein the gravity is obtained from the plurality of measurements of acceleration in a time period before a start of the sit-to-stand transfer only if a variance of the plurality of measurements of acceleration occurring in the time period is less than a threshold value.

19. The apparatus of claim 2, wherein the gravity is obtained from the plurality of measurements of acceleration in a time period before a start of the sit-to-stand transfer only if a range of the plurality of measurements of acceleration occurring in the time period is less than a threshold value.

* * * * *